United States Patent
Hellerqvist et al.

(10) Patent No.: US 6,476,002 B1
(45) Date of Patent: *Nov. 5, 2002

(54) TREATMENT OF CHRONIC INFLAMMATORY DISEASES WITH CM101/GBS TOXIN

(75) Inventors: Carl G. Hellerqvist, Brentwood; Barbara D. Wamil, Nashville, both of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/429,587

(22) Filed: Oct. 28, 1999

Related U.S. Application Data

(63) Continuation of application No. 08/790,989, filed on Jan. 29, 1997, now Pat. No. 6,028,060.

(51) Int. Cl.[7] .................. A61K 31/715; A61K 39/09; C07H 1/00
(52) U.S. Cl. .................. 514/54; 514/825; 514/886; 514/908; 536/123.1; 424/244.1
(58) Field of Search .................. 514/54, 908, 825, 514/886; 536/123.1; 424/244.1

(56) References Cited

U.S. PATENT DOCUMENTS

| | | |
|---|---|---|
| 4,242,326 A | 12/1980 | Sugawara et al. |
| 4,882,317 A | 11/1989 | Marbrug et al. |
| 4,895,838 A | 1/1990 | McCluer et al. |
| 5,010,062 A | 4/1991 | Hellerqvist et al. |
| 5,225,331 A | 7/1993 | Jennings et al. |
| 5,302,386 A | 4/1994 | Kasper et al. |
| 5,382,514 A | 1/1995 | Passaniti et al. |
| 6,028,060 A | * 2/2000 | Hellerqvist et al. ........... 514/54 |

FOREIGN PATENT DOCUMENTS

| | | |
|---|---|---|
| EP | 0 445 280 B1 | 9/1991 |
| WO | WO 94/10202 | 5/1994 |
| WO | WO 94/20085 | 9/1994 |
| WO | WO 96/25171 | 8/1996 |
| WO | 97/41844 | 11/1997 |
| WO | 98/14603 | 4/1998 |

OTHER PUBLICATIONS

Arbiser, J. L., M.D., Ph.D., *Angiogenesis and the Skin: A Primer, J. of the American Academy of Dermatology*, 34(3):486–497, (1996).

Augustin, H. G., et al., *Ovarian Angiogenesis: Phenotypic Characterization of Endothelial Cells in a Physiological Model of Blood Vessel Growth and Regression, Am. J. Pathol.*, 147(2):339–351, (1995).

Battegay, E. J., *Angiogenesis: Mechanistic Insights, Neovascular Diseases, and Therapeutic Prospects, J. Mol. Med.*, 73:333–346, (1995).

Braverman, I.M., M.D., et al., *Role of the Microcirculation in the Treatment and Pathogenesis of Psoriasis, The Journal of Investigative Dermatology*, 78(1):12–17, (1982).

Brem, H., et al., *Analysis of Experimental Antiagiogenic Therapy, Journal of Pediatic Surgery*, 28(3):445–451, (1993).

(List continued on next page.)

Primary Examiner—James O. Wilson
Assistant Examiner—Everett White
(74) Attorney, Agent, or Firm—Cooley Godward LLP

(57) ABSTRACT

A method of treating a chronic inflammatory disease such as rheumatoid arthritis or psoriasis includes treating a patient with a toxin derived from Group B β-hemolytic Streptococcus bacteria. The purified GBS toxin, or CM101, may be administered. intravenously to the patient in repeated doses.

25 Claims, 7 Drawing Sheets

OTHER PUBLICATIONS

Brem, H., et al., *Suppression of Tumor Metastasis by Angiogenesis Inhibition*, Surgical Forum, XLII:439–441, (Oct.–1991).

Brem et al., *Time Dependent Suppression of Wound Healing With the Angiogenesis Inhibitor, AGM–1470*, J. Cell Biol., 115:403a, (1991).

Brown, L. F., et al., *Increased Expression of Vascular Permeability Factor (Vascular Endothelial Growth Factor) in Bullous Pemphigoid, Dermatitis Herpetiformis, and Erythema Multiforme*, J. Invest. Dermatol., 104(5):744–749, (1995).

Brown, L. F., et al., *Overexpression of Vascular Permeability Factor (VPF/VEGF) and its Endothelial Cell Receptors in Delayed Hypersensitivity Skin Reactions*, J. Immunol., 154(6):2801–2807, (1995).

Caulfield, J.P., M.D., et al., *Morphologic Demonstration of Two Stages in the Development of Type II Collagen–Induced Arthritis*, Laboratory Investigation, 46(3):321–343, (1982).

Colville–Nash, P.R., et al., *Angiogenesis and Rheumatoid Arthritis: Pathogenic and Therapeutic Implications*, Annals of the Rheumatic Diseases, 51:919–925, (1992).

Courtenay, J.S., et al., *Immunisation Against Heterologous Type II Collagen Induces Arthritis in Mice*, Nature, 283:666–668, (1980).

D'Amato, Robert M.D., Ph.D., *Critical Components of the Female Reproductive Pathway are Suppressed by the Angiogenesis Inhibitor AGM–1470*, I.B.C. Conference (1996).

Detmar, M., et al., *Overexpression of Vascular Permeability Factor/Vascular Endothelial Growth Factor and its Receptors in Psoriasis*, J. Exp. Med., 180:1141–1146, (1994).

Dvorak, H. F., et al., *Vascular Permeability Factor/Vascular Endothelial Growth Factor, Microvascular Hyperpermeability, and Angiogenesis*, Am. J. Pathol., 146(5):1029–1039, (1995).

Dvorak, H. F., et al., *Vascular Permeability Factor/Vascular Endothelial Growth Factor: An Important Mediator of Angiogenesis in Malignancy and Inflammation*, Int. Arch. Allergy Immunol., 107:233–235, (1995).

Ferrara, N., *The Role of Vascular Endothelial Growth Factor in Pathological Angiogenesis*, Breast Cancer Res. Treat., 36:127–137, (1995).

Ferrara, N., et al., *Vascular Endothelial Growth Factor, a Specific Regulator of Angiogenesis*, Curr. Opin. Nephrol. Hypertens., 5(1):35–44, (1996).

Folkman, J., et al., *Angiogenic Factors*, Science, 235:442–447, (1987).

Folkman, J., *Angiogenesis in Cancer, Vascular, Rheumatoid and Other Disease*, Nature Medicine, 1(1):27–31, (1995).

Folkman, J., *Diagnostic and Therapeutic Applications of Angiogenesis Research*, C.R. Acad. Sci. Paris, Sciences de la vie, 316:914–918, (1993).

Gallin, J., et al. *Inflammation: Basic Principles and Clinical Correlates*, Chapter 40, Raven Press (1992), pp. 832–833.

Gordon, D.A., et al., *Rheumatoid Arthritis, Clinical Features: Early, Progressive and Late Disease*, Rheumatology, 4.1–4.3, Klippel and Dieppe, eds., Mosby, publ., (1994).

Hellerqvist, C.G., et al., *CM101 Induces a Complement–Activated Inflammatory Response Targeting Tumor Neovasculature*, Proceedings of the American Assoc. for Cancer Research, 37, Abstract #3328, (1996).

Hellerqvist, C.G., et al., *Studies on Group B β–Hemolytic Streptococcus I. Isolation and Partial Characterization of an Extra–Cellular Toxin*, Pediatr. Res., 12:892–898, (1981).

Hellerqvist, C.G., et al., *Antitumor Effects of GBST Toxin: A Polysaccharide Exotoxin From Group B β–Hemolytic Streptococcus*, J. Canc. Res. Clin. Oncol., 120:63–70, (1993).

Hellerqvist, C.G., et al., *Early Results of a Phase I Trial of CM101 in Cancer Patients*, Proceedings of the American Assoc. of Cancer Research Annual Meeting, 36:224, (1995).

Hellerqvist, C.G., et al., *Cytokine Production in Cancer Patients Receiving the Anti–Neovascularization Drug CM–101*, Proceedings of ASCO, Abstract #1592, vol. 14, (1995).

Hellerqvist et al., *Preliminary results of a Phase I trial of CM101 in cancer patients*, J. of Cellular Biochemistry, Supp 19B, p. 26 (1995).

Herblin, W., et al.,*Inhibition of Angiogenesis as a Strategy for Tumor Growth Control*, Molecular and Chemical Neuropathology, 21:329–336, (1994).

Hirata, S., et al., *Inhibition of In Vitro Vascular Endothelial Cell Proliferation and In Vivo Neovascularization by Low–Dose Methotrexate*, Arthritis and Rheumatism, 32(9):1065–1073, (1989).

Ingber, D., et al., *Synthetic Analogues of Fumagillin that Inhibit Angiogenesis and Suppress Tumour Growth*, Nature, 348:555–557, (1990).

Iwaguchi, T.,*Angiogenesis and Its Regulation*, Gan–To–Kagaku–Ryoho, 20:1–9 (1993).

Jennings, H. J., et al., *Structural Determination and Serology of the Native Polysaccharide Antigen of Type–III Group B Streptococcus*, Canadian J. of Biochemistry, 58(2):112–120, (1980).

Kim, K.J., et al., *Inhibiton of Vascular Endothelial Growth Factor–Induced Angiogenesis Suppresses Tumour Growth In Vivo*, Nature, 362:841–844, (1993).

Kimball, E.S., et al., *Angiogenesis in Pannus Formation*, Agents and Actions, 34(3/4):329–331, (1991).

Klagsbrun, M.,*Regulators of Angiogenesis*, Annu. Rev. Physiol., 53:217–239, (1991).

Kovacs, et al., *Fibrogenic cytokines and connective tissue production*, FASEB J. for Experimental Biology, 8(11):854–861 (1994).

Kusaka, M., et al., *Potent Anti–Angiogenic Action of AGM–1470: Comparision to the Fumagillin Parent*, Biochemical and Biophysical Res. Communications, 174(3):1070–1076, (1991).

Lawrence, R.C., *Classification and Epidemiology*, Rheumatology, 3.2–3.3, Klippel and Dieppe, eds., Mosby, publ., (1994).

Liote, F., *Synovial Angiogenesis*, Rev. Prat., 43(17):2239–2245, (1993).

Malhotra, R., et al., *Angiogenic Properties of Normal and Psoriatic Skin Associate with Epidermis, Not Dermis*, Laboratory Investigation, 61(2):162–165, (1989).

Matsubara, T., et al., *Inhibition of Human Endothelial Cell Proliferation In Vitro and Neovascularization In Vivo by D–Penicillamine*, J. Clin. Invest., 83:158–167, (1989).

Moses, M. A., et al., *Identification of an Inhibitor of Neovascularization From Cartilage*, Science, 248:1408–1410, (1990).

Moses, M.A., *A Cartilage–derived Inhibitor of Neovascularization and Metalloproteinases*, Clin. and Experimental Rheumatology, 11(Suppl. 8):S67–S69, (1993).

Nickoloff, B.J., et al., *Aberrant Production of Interleukin–8 and Thrombospondin–1 Psoriatic Keratinocytes Mediates Angiogenesis,* American Journal of Pathology, 144(4):820–828, (1994).

Oliver, S.J., et al., *Suppression of Collagen–Induced Arthritis Using an Angiogenesis Inhibitor, AGM–1470, and a Microtubule Stabilizer, Taxol,* Cellular Immunology, 157:291–299, (1994).

Ondrick, K., Ph.D., et al., *Angiogenesis,* Clinics in Podiatric Medicine and Surgery, 9(1):185–203, (1992).

Ono, M., et al., *Induction of Human Microvascular Endothelial Tubular Morphogenesis by Human Keratinocytes: Involvement of Transforming Growth Factor–I,* Biochem. Biophys. Res. Commun., 189(2):601–609, (1992).

Parkinson, D. R., *Present Staus of Biological Response Modifiers in Cancer,* The Amer. J. of Medicine, 99(Suppl.6A):54S–56S, (1995).

Peacock, D.J., et al., *An Angiogenesis Inhibitor in Combination with Anti–CD5 Mab Suppresses Established Collagen Induced Arthritis Significantly More Than Single Agent Therapy,* Arthritis and Rheumatism, 35(9), Abstract #B141, (1992).

Peacock, D.J. et al., *A Novel Angiogenisis Inhibitor Suppreses Rat Adjuvant Arthritis,* Arthritis and Rheumatism, 35(9), Abstract #101, (1992).

Peacock, D.J., et al., *Angiogenesis Inhibition Suppresses Collagen Arthritis,* J. Exp. Med., 175:1135–1138, (1992).

Plate, K. H., et al., *Molecular Mechanisms of Developmental and Tumor Angiogenesis,* Brain Pathol., 4:207–218, (1994).

Polverini, P.J, *The Pathophysiology of Angiogenesis,* Crit. Rev. Oral Biol. Med., 6(3):230–247, (1995).

Sato, N., et al,. *Actions of TNF and IFN–K on Angiogenesis In Vitro,* J. of Investigative Dermatology, 95(6 supp):85S–89S, (1990).

Senger, D. R., et al., *Vascular Permeability Factor (VPF, VEGF) in Tumor Biology,* Cancer and Metastasis Reviews, 12:303–324, (1993).

Senger, D. R., et al., *Vascular Permeability Factor, Tumor Angiogenesis and Stroma Generation,* Invasion Metastasis, 14:385–394, (1994–1995).

Staines, N.A., et al., *Collagen Arthritis—What Can it Teach us?,* British Journal of Rheumatology, 33:798–807, (1994).

Takamiya, Y., M.D., et al., *Inhibition of Angiogenesis and Growth of Human Nerve–Sheath Tumors by AGM–1470,* J. Neurosurg, 78:470–476, (1993).

Trentham, D.E., et al., *Autoimmunity to Type II Collagen: An Experimental Model of Arthritis,* The Journal of Experimental Medicine, 146:857–868, (1977).

Wamil, B. D., et al., *Leukocyte Activation in Response to CM104 Treatment of Cancer Patients,* Proceedings of the American Assoc. for Cancer Research, 37, Abstract #3329, (Mar. 1996).

\* cited by examiner

TREATMENT OF CHRONIC INFLAMMATORY DISEASES WITH CM101/GBS TOXIN

CROSS-REFERENCE TO RELATED APPLICATION

This application is a continuation of U.S. Ser. No. 08/790,989, filed Jan. 29, 1997 now U.S. Pat. No. 6,028,060.

FIELD OF THE INVENTION

This invention relates to the treatment of chronic inflammatory diseases, including rheumatoid arthritis and psoriasis.

BACKGROUND

Chronic inflammatory diseases such as rheumatoid arthritis (RA) and psoriasis are debilitating diseases affecting millions of people.

RA is a systemic, chronic, inflammatory disease affecting approximately 1–2% of the world's population. The manifestations of RA are usually most severe in the joints. The most frequently affected joints are the proximal interphalangeal and metacarpophalangeal joints in the hands and the metatarsophalangeal joints in the feet. The shoulders, elbows, knees, ankles, and wrists are also common targets of RA. Joints affected by RA ("active" joints) are characteristically tender. Accordingly, RA sufferers often experience pain and impaired mobility. While the severity and progression of RA vary considerably among affected individuals, RA patients as a group have twice the mortality rate of their unaffected counterparts. This decrease in life expectancy appears to be due in part to the side effects of current RA treatments.

In the initial stages of RA, the synovium of the affected joint becomes enlarged and inflamed. Expansion of the synovium is accompanied by angiogenesis and neovascularization. This, in turn, facilitates infiltration into the area by plasma cells, lymphocytes, and macrophages. As inflammatory cells accumulate within it, the synovium becomes edematous and hyperplastic. Neutrophils infiltrate the synovial fluid and cluster on the surface of the synovium. Fibrin deposition also occurs in the joint space. The synovial fluid increases in volume and turbidity with the accumulation of neutrophils, mononuclear cells and occasional red blood cells.

Chronic inflammation causes the synovium to thicken and extend over the articular surface, forming villi which project into the joint space. This aberrant and highly vascularized structure is called a pannus. The pannus invades and erodes the underlying cartilage, with the most active cartilage destruction occurring at the interface between pannus and cartilage. Cartilage destruction is effectuated by collagenase and metallo-proteinases secreted by the inflammatory cells of the pannus. Erosion eventually extends to the subchondral bone, articular capsule and ligaments. Osteoclastic molecules released by the inflammatory cells and synoviocytes allow the synovium to penetrate into the bone and form juxto-articular erosions, subchondral cysts, and osteoporosis.

After the cartilage has been destroyed, the pannus fills the entire joint space, laying down fibrous bands which bridge the opposing bones. As this fibrous ankylosis becomes calcified, a resulting bony ankylosis forms which fuses the opposing bones and prevents the joint from functioning.

RA is an autoimmune disease wherein patients have antinuclear antibodies and antibodies directed at autologous proteins such as immunoglobulin G (IgG), collagen, and cytoskeletal filamentous proteins. Rheumatoid factors (RFs) are autoantibodies found in serum and synovial fluid which bind to the Fc portion of IgG. RFs have been implicated in the pathogenesis of RA. When RFs bind IgGs, complement-activating immune complexes are formed. Activated complement causes the release of vasoactive and chemotactic substances which attract neutrophils and macrophages to the immune complex. As these cells ingest and destroy the immune complexes, they release molecules which cause inflammation and protein degradation and which attract other cells that contribute to RA pathogenesis. Because RFs are synthesized in joints and RFs of the IgG class are self-associating, immune complexes are frequently localized to joints. Nevertheless, immune complexes do circulate in some patients and are thought to cause the extra-articular manifestations of RA such as rheumatoid nodules, reactive amyloidosis and acute vasculitis.

The evidence that RA has autoimmune origins is supported by the finding that injecting avian type II collagen into rats or mice causes them to develop antibodies that recognize the rodent's endogenous collagen. The resulting auto-immune response, which is known as "collagen arthritis," mimics the physiological symptoms of RA such as joint inflammation (Trentham et al., *Autoimmunity to type II collagen: an experimental model of arthritis, J. of Experimental Medicine,* 146: 857 (1977); Courtenay et al., *Nature,* 283: 666). Collagen arthritis is a well established model system for the study of RA (Staines & Wooley, *Collagen arthritis-what can it teach us?, British Journal of Rheumatology,* 1994, 33: 798 (1994)).

The primary method for treating RA is through the administration of drugs which suppress the immune system or reduce inflammation. The two main classes of inflammation inhibitors are corticosteroids and non-steroidal anti-inflammatory drugs (NSAIDs).

Corticosteroids are not favored RA medications because, although they can achieve dramatic short-term improvements in RA, long-term treatment is not advisable due to serious side effects and diminished effectiveness of the drug. Short-term corticosteroid treatment is also far from ideal because arthritis symptoms rapidly reappear, often with increased severity, after treatment has stopped. Although corticosteroids such as prednisone can suppress clinical symptoms of RA, the drugs do not prevent RA-mediated joint destruction. Furthermore, typical corticosteroid side effects include: peptic ulcer, hypertension, diabetes mellitus, and glaucoma.

NSAIDs such as aspirin, ibuprofen, and indomethacin are frequently prescribed for RA. Although these drugs can reduce swelling in active joints by inhibiting prostaglandin synthesis, their poor penetration of joint spaces necessitates administration of high doses, and such high doses tend to cause gastrointestinal irritation, ulceration, and bleeding. NSAIDs affect prostaglandin-regulate processes not associated with the inflammation process. NSAIDs are also potent renal toxins, and so are also inadequate for treatment of RA.

Patients with severe active RA may be treated with immunosuppressants such as cyclophosphamide, methotrexate, and azathioprine. While they can reduce inflammation, these drugs affect the patient's entire immune system and have serious side effects including liver disease, bone marrow suppression, and increased risk of malignancy.

Other RA medications include penicillamine, chloroquine, hydroxychloroquine, and gold salts. All have potentially serious side effects. D-penicillamine can cause bone marrow suppression, proteinuria, and nephrosis. Deaths resulting from penicillamine treatment have also been reported. Patients treated with hydroxychloroquine or chloroquine must be monitored for signs of irreversible retinal damage. Gold can induce toxic reactions in the form of dermatitis, renal failure or hepatitis, and its efficacy at treating arthritis is questionable.

Psoriasis sufferers include approximately 1–3% of the population in the United States and an even higher percentage of Northern Europeans. Psoriasis is a chronic inflammatory skin disease in which the patient's skin exhibits' recurrent erythematous plaques. These appear as white or silvery, scaling lesions on the skin, especially in the area of the scalp, elbows, knees, back, and buttocks. The accompanying burning and itching may cause discomfort. In severe forms, severe arthritis or exfoliation develops, as well.

The psoriatic lesions exhibit epidermal hyperplasia, infiltration of inflammatory cells, and abnormalities of dermal capillary networks. They are believed to result from epithelial cell hyperproliferation, neovascularization, and, of course, the infiltration of inflammatory cells into the area. Angiogenesis is believed to be necessary to maintain the inflammation and direct neutrophils and lymphocytes into the psoriatic lesion. Additionally, psoriasis patients have autoantibodies directed at the stratum corneum. These autoantibodies are implicated in the pathogenesis of the disease.

Current treatment for psoriasis includes lubricating creams or oils, keratolytics, and topical corticosteroids. For severe forms of the disease, methotrexate may be given, but its high potential for toxicity requires rigidly controlled treatment conditions, including careful monitoring of hematologic, renal, and hepatic function. Treatment for psoriatic arthritis is similar to that for RA, with some exceptions. For example, antimalarials may aggravate the underlying psoriasis.

RA and psoriasis are diseases characterized by unregulated angiogenesis. Vascular endothelial growth factor (VEGF) has been implicated in driving such unregulated angiogenesis by stimulating endothelial cells lining nearby microvessels to proliferate and begin the process leading to new blood vessel formation. There is evidence that VEGF receptors are overexpressed by endothelial cells that line the blood vessels supplying the inflammatory reactions leading to these disorders. (Dvorak, *Int. Arch. Allergy. Immunol.*, May-June 1995).

What is needed is a treatment method for chronic inflammatory diseases such as RA and psoriasis. There is a need for a compound which inhibits the signs and symptoms of these diseases, and particularly reduces the pain, inflammation, joint swelling, and lesions associated with these diseases. Furthermore, what is needed is a treatment method, and particularly a compound, which is easy to administer and which is nontoxic.

SUMMARY OF THE INVENTION

One aspect of the present invention is a method for treating patients with chronic inflammatory diseases, such as RA and psoriasis, by administering CM101, a bacterial polysaccharide that is generally nontoxic, to the patient in order to reduce the likelihood of formation of new blood vessels.

RA patients treated with CM101 experience reduction of pain, joint swelling, and acute inflammation, and also experience inhibition of pannus formation. CM101 may be administered before the onset of RA, when the first symptoms of RA are detected, and/or at later stages in RA progression.

Psoriasis patients treated with CM101 also experience reduction of the signs and symptoms of their disease. In addition to the improvement of the associated psoriatic arthritis, there is a reduction in the size and occurrence of psoriatic lesions and associated discomfort. As with treatment for RA, CM101 may be administered at various stages of the disease.

Another aspect of the present invention is a kit and a method of making a kit having a GBS toxin, preferably CM101, in a pharmaceutical composition along with instructions of how to administer the toxin for treatment of chronic inflammatory diseases.

The administration of CM101 to patients suffering from chronic inflammatory diseases has great utility, specifically in inhibiting the development of RA, reducing joint inflammation in RA patients, and reducing neovascularization in synovial tissues. Furthermore, the method of the present invention has great utility in inhibiting the development of psoriasis and psoriatic arthritis, and particularly in reducing the likelihood of formation of abnormal vasculature which facilitates the inflammatory reactions causing the lesions. Other chronic inflammatory diseases that are characterized by angiogenesis may also be advantageously treated.

DETAILED DESCRIPTION OF THE INVENTION

Figure 1:
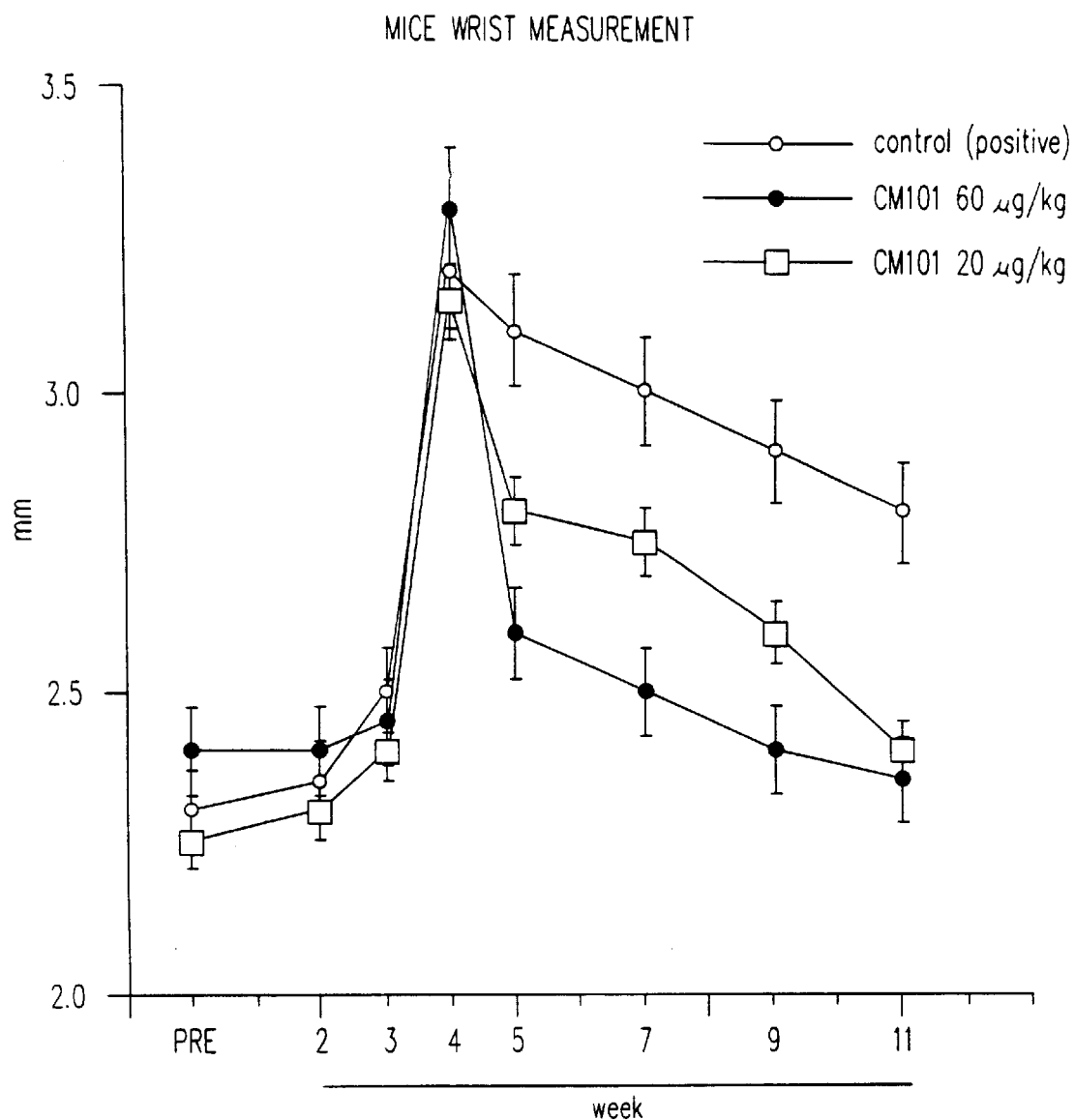
FIG. 1 charts the wrist joint diameters of collagen arthritis-afflicted mice over time. The mice received 20 $\mu$g/kg CM101, 60 $\mu$g/kg CM101, or saline solution. CM101 treatment started on week 4 and continued through week 9. Measurements were taken prior;to the start of the experiment (PRE) and at 2, 3, 4, 5, 7, 9 and 11 weeks.
Figure 2:
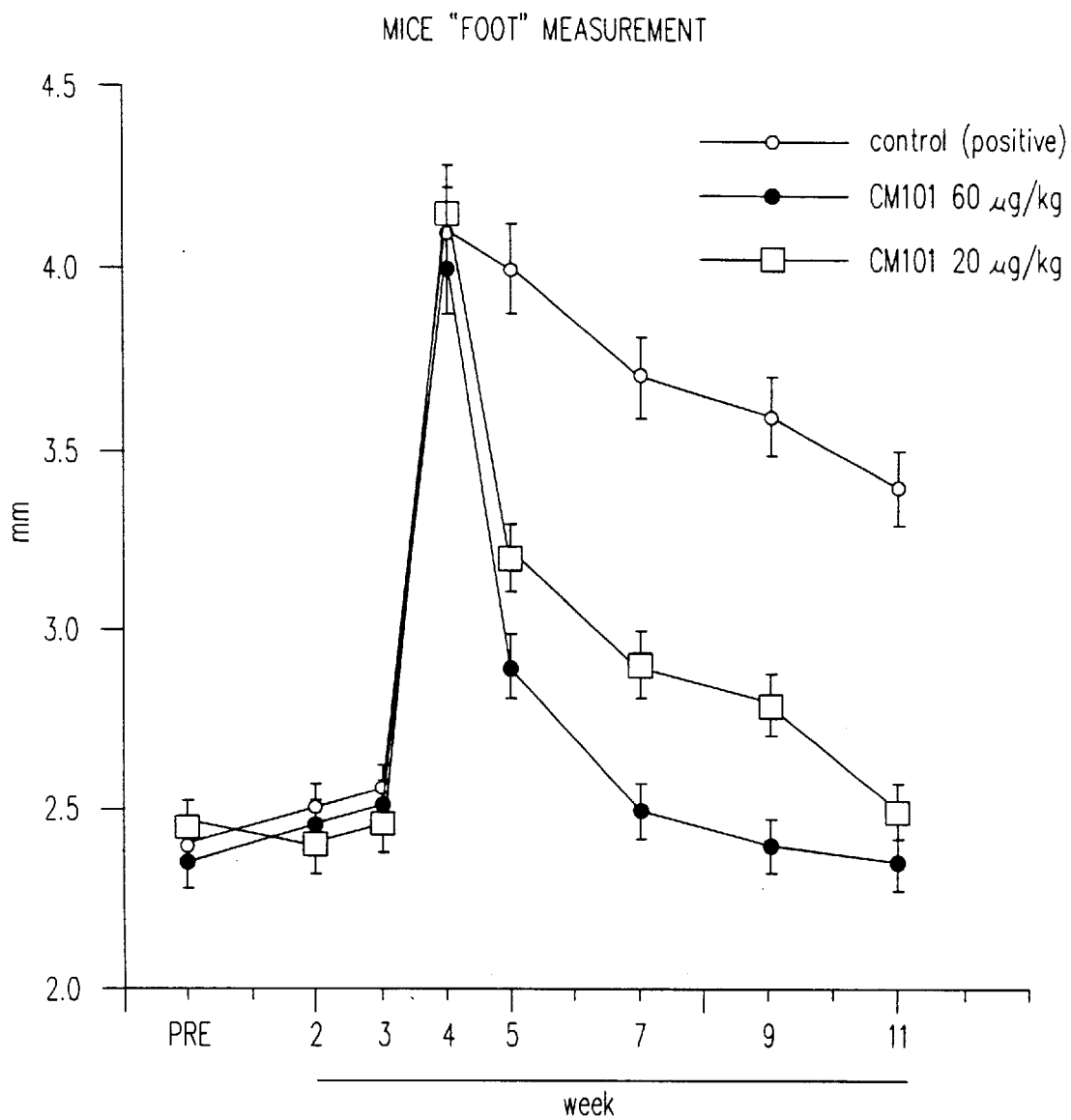
FIG. 2 charts the foot joint diameters of collagen arthritis-afflicted mice over time. The mice received 20 $\mu$g/kg CM101, 60 $\mu$g/kg CM101, or saline solution. CM101:treatment started on week 4 and continued through week 9. Measurements were taken prior to the start of the experiment (PRE) and at 2, 3, 4, 5, 7, 9, and 11 weeks.
Figure 3:
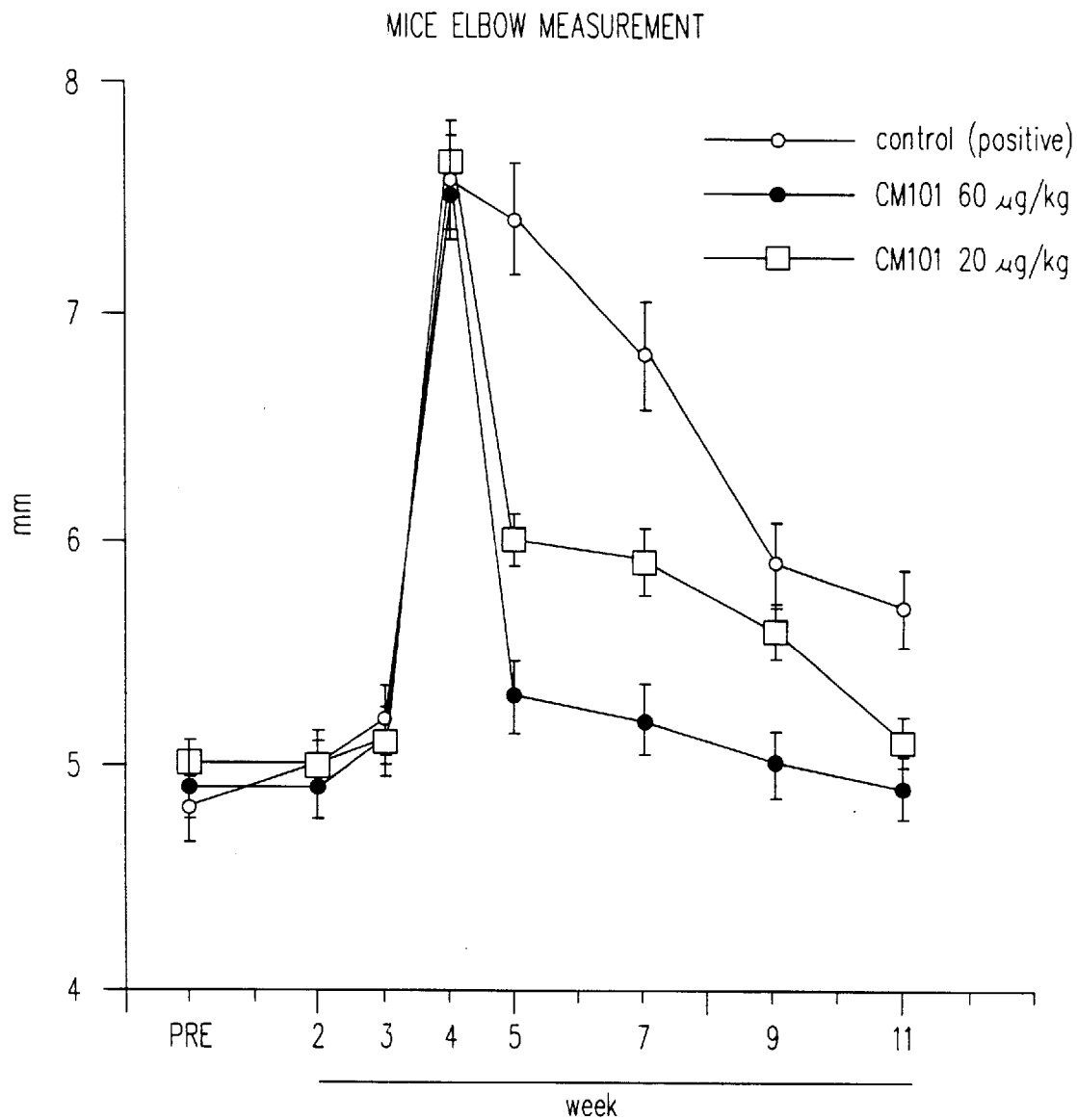
FIG. 3 charts the elbow joint diameters of collagen arthritis-afflicted mice over time. The mice received 20 $\mu$g/kg CM101, 60 $\mu$g/kg CM101, or saline solution. CM101 treatment started on week 4 and continued through week 9. Measurements were taken prior to the start of the experiment (PRE) and at 2, 3, 4, 5, 7, 9, and 11 weeks.
Figure 4:
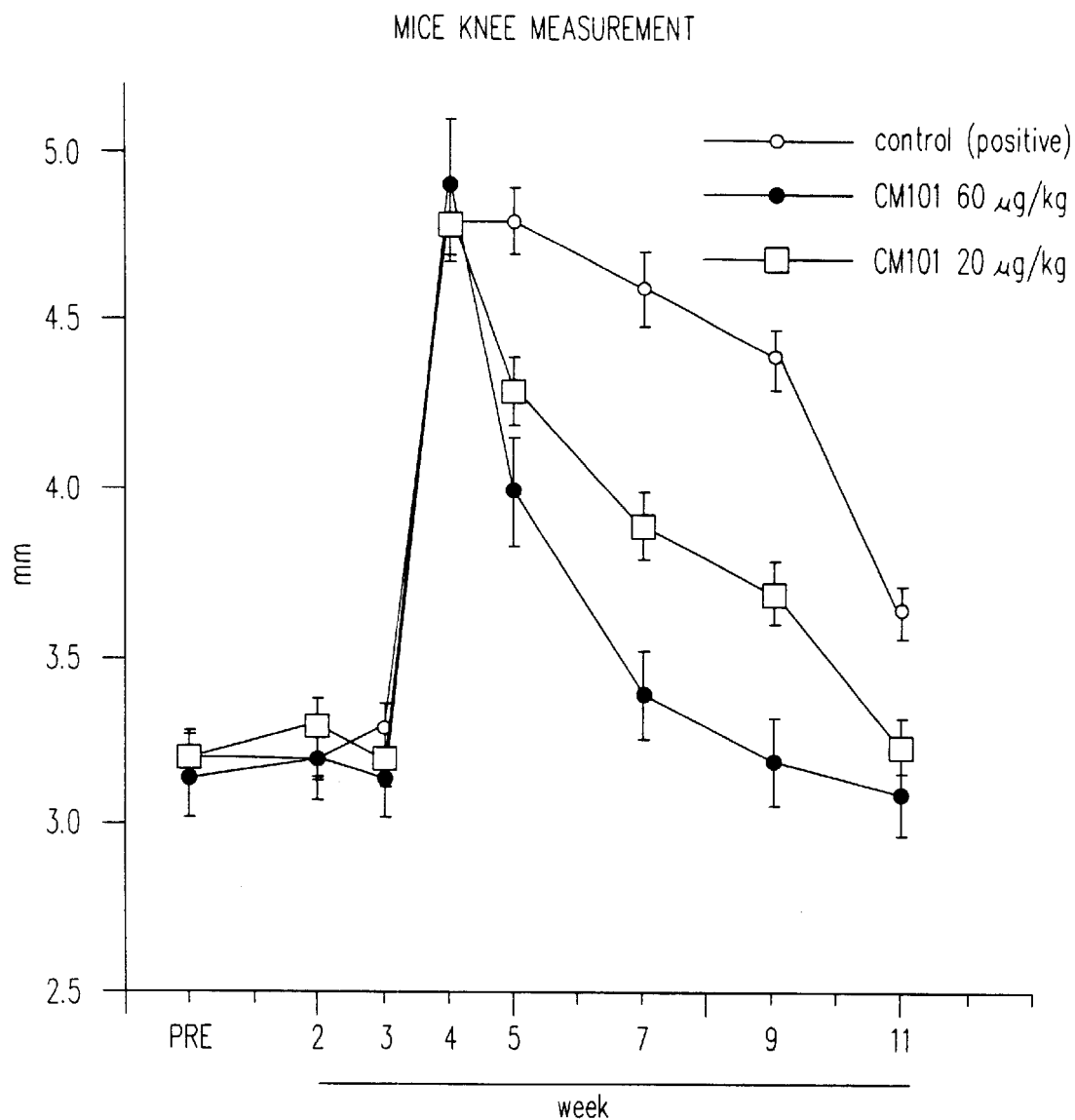
FIG. 4 charts the knee joint diameters of collagen arthritis-afflicted mice over time. The mice received 20 $\mu$g/kg CM101, 60 $\mu$g/kg CM101, or saline solution. CM101 treatment started on week 4 and continued through week 9. Measurements were taken prior to the start of the experiment (PRE) and at 2, 3, 4, 5, 7, 9, and 11 weeks.

CM101, a GBS toxin, is a polysaccharide molecule isolated from group B β-hemolytic Streptococcus (GBS). Specifically, pathogenic group B β-hemolytic streptococcus produces a polysaccharide exotoxin. This exotoxin is the putative agent for a condition known as GBS pneumonia or "early-onset disease," which is characterized by sepsis, granulocytopenia, and respiratory distress, i.e. pulmonary hypertension and proteinaceous pulmonary edemia (Hellerqvist, C. G. et al., *Studies on group B β-hemolytic* streptococcus I. Isolation and partial characterization of an extra-cellular toxin., Pediatr. Res., 12:892–898 (1981)). It is believed that only newborn infants are susceptible to early onset disease because receptors for CM101 are present primarily on the lungs of newborns but that the receptors are lost approximately four to seven days after birth. CM101 is not known to cause toxicity in older humans. Isolated and purified CM101 has been shown to have toxic effects on sheep experimental models that mimic GBS infant pneumonia (Hellerqvist, C. G. et al., Studies on group B β-hemolytic streptococcus I. Isolation and partial characterization of an extra-cellular toxin., Pediatr. Res., 12:892–898 (1981)). In the sheep model for neonatal early onset disease, GBS toxin causes pulmonary hypertension, increased pulmonary vascular permeability, granulocytopenia, and pulmonary sequestration of granulocytes.

CM101 has a molecular weight of approximately 300,000 Daltons and comprises N-acetyl-galactosamine, N-acetyl-glucosamine, glucose, galactose, and mannose residues. Carboxylic acid residues are also believed to be an integral part of the molecule. Repeating active epitopes most likely play an important role in the pathophysiological response to CM101 by crosslinking receptors on target endothelium (Hellerqvist, C. G. et al., Early Results of a Phase I Trial of CM101 in Cancer Patients., Proceedings of the American Association of Cancer Research Annual Meeting 36:224 (1995)).

A method of purification of a GBS toxin is provided in U.S. Patent No. 5,010,062. Preferably, however, the CM101 is purified according to the method taught in U.S. Pat. No. 5,811,403, copending incorporated herein by reference.

A source for GBS starting material for use in the method of the present invention may be obtained by culturing strains of Group B β-hemolytic Streptococcus bacteria that have recently infected or are capable of infecting newborn infants. Isolates of such strains may be obtained from the blood or cerebral spinal fluid of infected infants.

GBS toxin as used herein is defined as any fraction or component isolated from natural or lysed GBS bacteria, or derived from media supernatants of lysed and/or autoclaved GBS bacteria, and which has a biological activity as evidenced by induction of respiratory distress in the sheep assay (Hellerqvist, C. G. et al., Studies on group B β-hemolytic streptococcus I. Isolation and partial characterization of an extra-cellular toxin., Pediatr. Res., 12:892–898 (1981)) or activation of complement and binding to neovasculature as demonstrated by a peroxidase-antiperoxidase (PAP) assay of a tumor tissue specimen (Hellerqvist, C. G. et al., Anti-tumor effects of GBS toxin: a polysaccharide exotoxin from group B β-hemolytic streptococcus, J. Canc Res. Clin. Oncol., 120:63–70 (1993); and Hellerqvist, C. G. et al., Early Results of a Phase I Trial of CM101 in Cancer Patients., Proceedings of the American Association of Cancer Research Annual Meeting, 36:224 (1995)). GBS toxin also means any synthetic polysaccharide with the same structure or function as any GBS-derived molecule with the aforementioned activity.

Substantially pure GBS toxin means a preparation in which GBS toxin is greater than 40% pure (e.g., present in a concentration of at least about 40% by weight), preferably at least approximately 60% pure, more preferably at least approximately 90% pure, and most preferably at least approximately 95% pure. The dosages described herein are for 95% pure GBS toxin. Dosages of lower purity GBS toxin should be altered accordingly. The purity of GBS toxin is discussed in greater detail in U.S. Pat. No. 5,811,403.

Rheumatoid arthritis or RA as used herein includes any disease that meets the diagnosis criteria set forth by the American Rheumatism Association for rheumatoid arthritis. These criteria are presented in Table 1 which is adapted from Rheumatology, Klippel and Dieppe, eds., Mosby, publ. (1994). RA also includes variants of RA such as juvenile RA, Still's disease, or Felty's syndrome.

TABLE 1

1987 Revised Diagnostic Criteria for the Classification of Rheumatoid Arthritis

1. Morning stiffness of at least one hour.*
2. Arthritis in at least 3 joint areas (right or left proximal interphalangeal, metacarpophalangeal, wrist, elbow, knee, ankle and metatarsophalangeal joints) with swelling or fluid.*
3. Arthritis of hand joints (at least one area swollen in a wrist, metatarsophalangeal or proximal interphalangeal joint).*
4. Symmetric joint swelling and involvement.*
5. Subcutaneous nodules.
6. Radiographic changes typical of rheumatoid arthritis.
7. Positive rheumatoid factor.

*Specified criteria that must be present for at least 6 weeks.

Treatment of RA as used herein includes the prevention, amelioration, decreased severity, inhibited progression, alleviation or elimination of RA or the symptoms thereof. People who may be treated include persons who have been diagnosed with early stage RA. The criteria for diagnosing RA are listed in Table 1. Persons genetically or environmentally predisposed to developing RA may also be treated, particularly if they have elevated RF levels. RF levels can be measured by agglutination tests such as the latex fixation test or the bentonite tube dilution tests. A mammal is in need of CM101 treatment if the mammal has RA or has a propensity to develop RA.

Reduction in the symptoms of RA may be measured by observing the degree of joint swelling or pain, or by radiographic, ultrasound or magnetic resonance imaging of joint morphology. GBS toxin is particularly useful at reducing swelling. Also, heat is a symptom of RA, and the effectiveness of CM101 can therefore be measured by thermal photographs of joints.

Monitoring of CM101 can be achieved by measuring decreases in the level of CD4+cells. This can be achieved by flow cytometry. Monitoring for an increase in cytokine levels, such as tumor necrosis factor (TNF), IL-8, IL-6, IL-10, and macrophage inflammatory protein α (MIPα), is also possible. Furthermore, magnetic resonance imaging (MRI) is useful for visualizing vascularization and providing a relative measure of vessel density.

For the treatment of chronic inflammatory diseases, CM101 may be administered parenterally, topically, by internal injection of a bolus, by direct injection into affected joints, or by inhalation spray in dosage unit formulations containing conventional non-toxic pharmaceutically acceptable carriers, adjuvants and vehicles. The term parenteral as used herein includes subcutaneous, intradermal, or intraperitoneal injections as well as intravenous, intra-arterial, intramuscular, intrasternal injection or infusion techniques. Parenteral administration is preferable and intravenous administration is most preferable. While a single intravenous administration may last up to 120 minutes, 5 to 60 minutes is the preferable duration range and 5 to 30 minutes is the most preferable duration range.

For the treatment of chronic inflammatory diseases, CM101 is administered in doses of at least about 1 μg/kg of the patient's body weight, preferably between about 1 and about 100 µg/kg, more preferably between about 1 and about 50 µg/kg, most preferably between about 1 and about 25 µg/kg. It will be understood, however, that the specific dose level for any particular patient will depend on a variety of factors including the age, body weight, general health, sex, diet, and severity of the inflammation or the disease of the patient undergoing therapy as well as the time of administration and route of administration of CM101.

CM101 may be administered daily, semi-weekly, weekly, semi-monthly or at monthly intervals. Preferably, the interval will be in the range of one week to one month. Most preferably, the interval will be in the range of 7 days to 2 weeks. The severity of the patient's disease can be taken into account when determining appropriate intervals for CM101 treatments. The appropriate interval can also be determined by assaying the levels of mature granulocytes in the patient's blood. The level of mature granulocytes is relevant to the timing of CM101 treatment because CM101 may cause granulocyte activation and subsequent depletion if administered too frequently. Hence, future CM101 treatments may be more efficacious if the patient's supply of mature granulocytes has been replenished. One method for monitoring mature granulocyte levels is flow cytometry using the CD69 antigen to detect mature granulocytes.

CM101 treatments may continue over the course of several months, one year, several years, or for the duration of the patient's lifetime. Alternatively, CM101 may be administered on a one-time only basis provided that symptoms of the disease do not reappear. Preferably, the patient will have at least about 5, 10 or 15 treatments.

The CM101-mediated reduction in joint swelling may be monitored by external measurements of joint size, degree of tenderness upon palpation, degree of joint mobility, or radiological or other images of joint morphology. The CM101-mediated reduction of size, number, and degree of inflammation of psoriatic lesions will be evident upon visual observation.

CM101 should be administered in levels sufficient to reduce long-term pain in the body of the patient. The skilled artisan will appreciate that increasing doses of CM101 should be administered until the patient experiences pain reduction and additional CM101 fails to effect greater pain amelioration. Intravenous administration could be set up such that the patient can control future dosages of CM 101 according to the amount of pain they experience approximately 8 hours after a CM101 treatment.

Another aspect of the present invention is an article of manufacture, such as a kit, and a method for making the article of manufacture. The article includes a pharmaceutical composition comprising a GBS toxin, and particularly CM101, and a pharmaceutically acceptable carrier. The pharmaceutical composition may be placed in a suitable container, as is well known in the art. Also included are instructions for treatment of patients according to the methods of the present invention.

Without limitation to a particular theory, it is believed that GBS toxin, and especially CM101, operates as an antiangiogenic agent which prevents the formation of new blood vessels. CM101 inhibits angiogenesis by binding dedifferentiated endothelial cells, the cells that are stimulated by hypoxic conditions to form new blood vessels. CM101 facilitates the binding and opsonization by C3 of endothelial cells, and these cells become the target of inflammatory cells, ultimately leading to the destruction of the endothelial cells.

Angiogenesis plays a key role in the pathogenesis of RA because synovial hypoxia induces the release of VPGF which causes the dedifferentiation of endothelial cells and the formation of new blood vessels. Since the formation of these vessels is impeded by CM101 treatment, synovial tissue hyperplasia and lymphocyte infiltration are at least partially inhibited. As a result, the formation of new pannus is minimized, and existing pannus is reduced. These mechanisms are thought to underlie the CM101-mediated reduction in joint swelling, acute inflammation, fibrin deposition, and pannus formation demonstrated herein.

Angiogenesis also plays a key role in the pathogenesis of psoriasis because it facilitates the infiltration of neutrophils and lymphocytes into the psoriatic lesion. Since the formation of new blood vessels is impeded by CM101 treatment, the formation, maintenance, and enlargement of psoriatic lesions are impaired.

RA and psoriasis are both diseases characterized by inflammation. Because inflammation is detrimental to persons suffering from RA or psoriasis, respectively, and there is evidence that CM101 works by stimulating inflammation, it might be expected that CM101 treatment would exacerbate these diseases. Surprisingly, CM101 at least partially reduces the signs and symptoms of inflammatory diseases such as RA and psoriasis.

It has been reported that AGM-1470 is an antiangiogenic compound which reduces joint swelling in rats with collagen arthritis (Peacock et al., *Angiogenesis inhibition suppresses collagen arthritis, J. Exp. Med.,* 175:1135 (1992)). AGM-1470 is a synthetic analog of fumagillin, a naturally occurring fungal antibiotic derived from *Aspergillus fumigatus fresenius* (Ingber et al., *Synthetic analogues of fumagillin that inhibit angiogenesis and suppress tumour growth, Nature,* 348:555 (1990)). Since it is not a polysaccharide, AGM-1470 is structurally unrelated to CM101. The mechanism of action of AGM-1470 also differs from CM101: AGM-1470's angiogenic activity is reported to not require induction of the host's immune system (Brem & Folkman, *Analysis of experimental antiangiogenic therapy, J. Ped. Sury.,* 28:445 (1993)).

Another difference between AGM-1470 and CM101 is that AGM-1470 inhibits both physiological and pathological angiogenesis whereas CM101 only inhibits pathological angiogenesis. As their names suggest, pathological angiogenesis is associated with disease, and physiological angiogenesis occurs under normal, healthy circumstances. Wound healing, the female menstrual cycle, and pregnancy are examples of physiological angiogenesis (Brem & Folkman, *Analysis of experimental antiangiogenic therapy, J. Ped. Surp.,* 28:445 (1993)). Pathological angiogenesis occurs in diabetic retinopathy, hemangioma, cancer, psoriasis, RA, and osteoarthritis (Folkman et al., *Angiogenic factors, Science,* 235:442 (1987); Kimball et al., *Meeting report—angiogenesis in pannus formation, Aients & Actions,* 34:329 (1991)). Thus, in addition to its reported role in inhibiting angiogenesis in pathological conditions such as tumors and RA, AGM-1470 inhibits wound healing (Brem et al., *Time dependent suppression of wound healing with the angiogenesis inhibitor, AGM-1470, J. Cell Biol.,* 115: 403a (1991)) and female reproduction (D'Amato, Abstract from IBC Conference on Angiogenesis), a clearly undesired effect. By comparison, CM101 does not inhibit placental or endometrial growth. CM101 not only fails to inhibit wound healing, but has actually been shown to facilitate it, as evidenced by a copending application filed concurrently herewith. Therefore, CM101 can be administered to treat RA or psoriasis without causing the undesirable side effects of female infertility or compromised wound healing capacity that would result from AGM-1470 treatment.

The following examples are given for the purpose of illustrating the present invention and shall not be construed as being limitations on the scope or spirit of the instant invention.

EXAMPLES

Example 1

CM101 Treatment Reduces Joint Swelling

A mouse model for RA was utilized to assay the effects of CM101 on RA (Courtenay et al., *Immunisation against heterologous type II collagen induces arthritis in mice*, Nature 283: 666 (1980)). Male mice of the DBA/1 strain received intradermal injections of chicken Type II collagen at 4–6 sites on the back. The injected collagen was prepared as follows: 100 μg collagen was dissolved in 100 ml of 0. IM acetic acid and emulsified in an equal volume of Complete Freund's Adjuvant (0.5 mg/ml *M.butyricum*). Three weeks later, at week zero in the experiment, all animals were immunized by a single intraperitoneal injection of 100 μg collagen. Two weeks after initial collagen injection, all animals tested positive for anti-chicken collagen antibodies. This was used as a diagnosis of incipient collagen arthritis.

The antibody-positive animals were divided into two experimental groups and one positive control group. From week 4 through week 9,. all animals received intravenous 100 μl injections three times per week. For the mice in the first experimental group (n=10), each injection contained 20 μg/kg of CM101 dissolved in saline. For the second experimental group (n=10), 60 μg/kg of saline-dissolved CM101 was injected each time. The positive control group (n 10), which previously received collagen injections and tested positive for anti-collagen antibodies, received physiological saline injections instead of CM101.

Joint inflammation was recorded by measurement with a special spring-loaded caliper (Starrett #1015 MA2). Measurements were made prior to the commencement of the experiment (PRE) and at weeks 2, 3, 4, 5, 7, 9, and 11. Two days after the final treatment on week 9, eighteen animals from the different groups were sacrificed and their front and hind limbs were formalin-fixed and sectioned for histological analysis. The remaining animals were not sacrificed until their joint measurements were taken in week 11.

FIGS. 1, 2, 3 & 4 show the diameter measurements of the wrist, foot, elbow and knee joints, respectively, of CM101-treated mice and control mice.

Prior to the initial collagen injection (PRE), all mice had small diameter joints. The joint measurements of CM101-treated and control mice continued to be very similar in the weeks following the second round of collagen injections: joint diameters hovered around pre-treatment levels on weeks 2 and 3 and then increased tremendously between weeks 3 and 4. At week 4, the animals' joints were 35–70% larger than at the start of the experiment.

CM101 treatments began in week 4 and continued on a tri-weekly basis until week 9. During these weeks, the joint measurements of the animals which received CM101 were significantly smaller than the joint measurements of control mice, and the 60 μg/kg dose of CM101 appeared more effective than 20 μg/kg CM101 in reducing joint size.

Even though they did not receive CM101 treatments after week 9, the CM101-treated animals exhibited additional reduction in joint size between weeks 9 and 11. By week 11, the joint measurements of mice treated with 20 μg/kg CM101 or 60 μg/kg CM101 were quite similar—their joints were significantly smaller than the joints of control mice and had almost returned to their pre-experimentation size.

Thus, CM101 diminishes pre-existing joint swelling. While the 60 μ/kg dose reduces swelling more effectively than the 20 μg/kg dose over short periods of time, the two dosages have similar long-term efficacy. CM101's therapeutic role in alleviating joint swelling is also supported by results of a similar experiment in which collagen arthritis-afflicted mice were treated with 60 μg/kg or 240 μg/kg CM101 from weeks 2 through 9 (data not shown).

Example 2

CM101 Reduces Acute Inflammation and Pannus Formation.

The protocol described above was followed except that the CM101 was administered at dosages of 0 μg/kg, 60 μg/kg and 240 μg/kg in saline, and administration occurred three times a week from weeks 2 through 9. Histological sections were made 2 days after the final treatment at week 9.

Figure 5A:
FIG. 5 depicts cross-sections of the knee joint of a normal mouse (A), a:collagen arthritis-afflicted mouse (B), and a collagen arthritis-afflicted mouse treated with CM101 at 60 $\mu$g/kg (C).
Figure 5B:
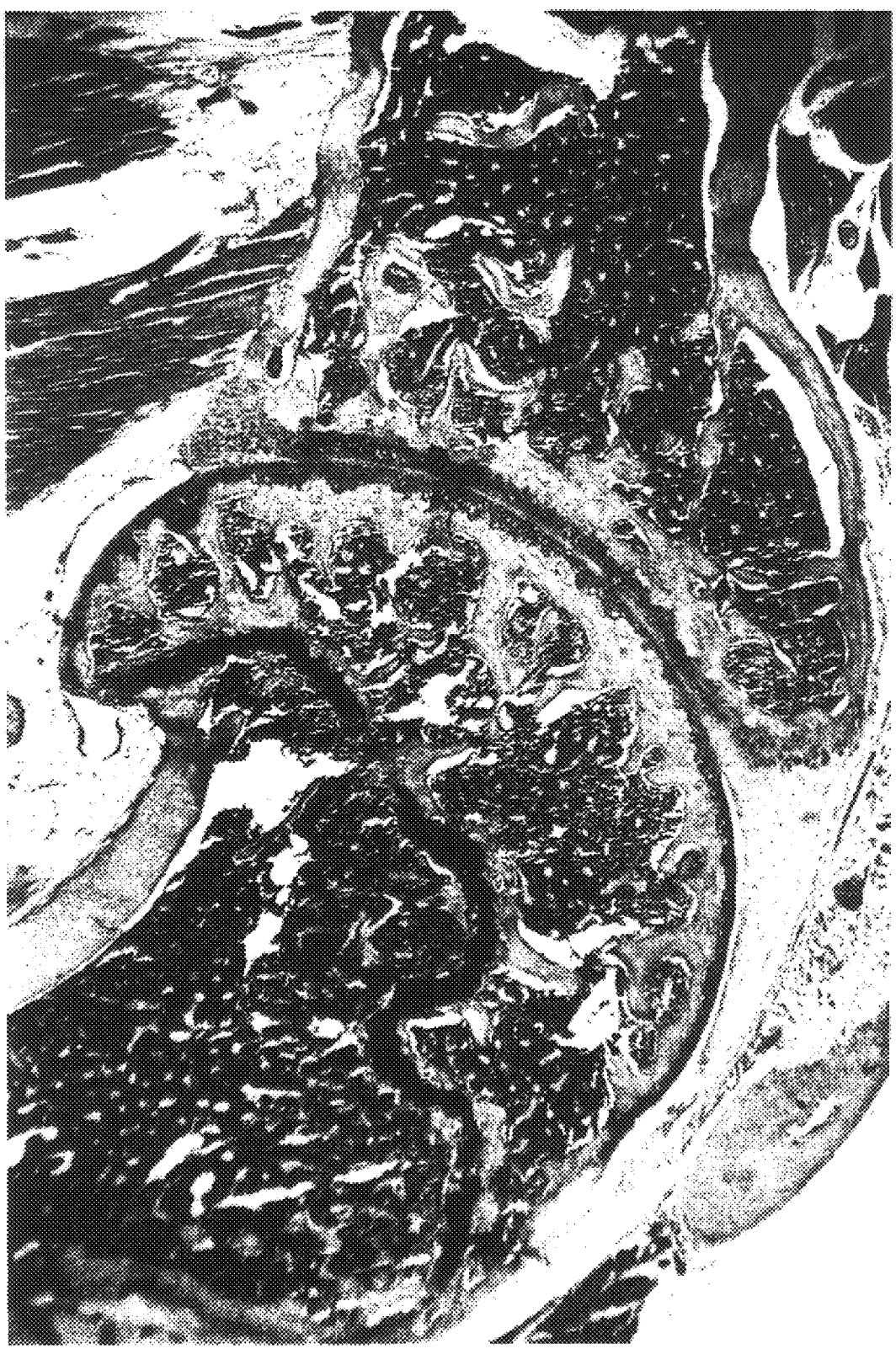
Figure 5C:

As shown in FIG. 5, CM101 diminishes the cellular manifestations of RA.

Under normal conditions (FIG. 5A), articular surfaces are curvilinear in shape and lined by a thin synovial membrane. Just below the synovium lies a thick, even layer of hyaline cartilage (which is darkly stained in these preparations). Under the hyaline cartilage is the subchondral bone.

The joint of a mouse with collagen arthritis (FIG. 5B) exhibits flattening of the articular surface, active inflammation in the joint space, synovial hypertrophy and hyperplasia, pannus formation, and mild ankylosis. Destruction of the underlying hyaline cartilage and bone, which was caused by the pannus, is evident.

Unlike its untreated counterpart, the joint of a CM101-treated mouse (FIG. 5C) lacks active inflammation and pannus formation. The hyaline cartilage layer is thick and even. The only morphological signs of arthritis are mild articular flattening, some loss of articular cartilage and subchondral bone, and fibrosis in the area where pannus would otherwise have been.

Thus, CM101 treatment reduces periarticular inflammation, pannus formation, erosion of cartilage and bone, and ankylosis.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for treating a patient with a chronic inflammatory disease, which method comprises:
   administering to the patient a polysaccharide toxin from Group B β-hemolytic Streptococcus (GBS) bacteria in a quantity sufficient to reduce formation of new blood vessels at a site of disease.

2. The method of claim 1 wherein the chronic inflammatory disease is angiogenesis dependent.

3. The method of claim 1 wherein the chronic inflammatory disease is selected from the group consisting of rheumatoid arthritis and psoriasis.

4. The method of claim 3 wherein the disease is psoriasis and the GBS toxin is administered in a quantity sufficient to diminish psoriatic lesions.

5. The method of claim 1 wherein the GBS toxin is substantially pure.

6. The method of claim 5 wherein the GBS toxin has a purity of at least approximately 90%.

7. The method of claim 1 wherein the GBS toxin is administered parenterally.

8. The method of claim 7 wherein the GBS toxin is administered intravenously.

9. The method of claim 1 wherein the patient is at least 4 days old.

10. The method of claim 9 wherein the patient is at least 7 days old.

11. The method of claim 1 wherein the treatment is maintained by repeatedly administering the GBS toxin to the patient at an interval in the range of one week to one month.

12. The method of claim 11 wherein the interval is in the range of 7 days to 2 weeks.

13. The method of claim 1 wherein the GBS toxin is administered at a level of 1 µg/kg to 100 µg/kg body weight of the patient.

14. The method of claim 13 wherein the GBS toxin is administered at a level of 1 µg to 25 µg/kg body weight of the patient.

15. The method of claim 1 wherein the GBS toxin is administered in a quantity sufficient to reduce pain in the body of the patient approximately 8 hours after the administration of the GBS toxin.

16. The method of claim 1 wherein the GBS toxin is administered in a quantity sufficient to reduce swelling in the joints of the body.

17. The method of claim 1 wherein the GBS toxin is administered in a quantity sufficient to inhibit angiogenesis in synovial tissues of the patient.

18. The method of claim 1 wherein the GBS toxin provides biological activity as evidenced by induction of respiratory distress in a sheep assay or activation of complement and binding to neovasculature in a peroxidase-antiperoxidase assay of a tumor tissue specimen.

19. A method for treating a patient having a chronic inflammatory disease that is angiogenesis dependent, which method comprises:
    administering to the patient a compound that reduces formation of new blood vessels at a site of disease but does not inhibit wound healing, wherein the compound is a polysaccharide toxin from Group B β-hemolytic Streptococcus (GBS) bacteria.

20. The method of claim 19 wherein the GBS toxin is substantially pure.

21. The method of claim 20 wherein the GBS toxin has a purity of at least approximately 90%.

22. The method of claim wherein the GBS toxin provides biological activity as evidenced by induction of respiratory distress in a sheep assay or activation of complement and binding to neovasculature in a peroxidase-antiperoxidase assay of a tumor tissue specimen.

23. A method for treating psoriasis in the body of a patient, which method comprises: administering to the patient a polysaccharide toxin from Group B β-hemolytic Streptococcus (GBS) bacteria in a quantity sufficient to reduce signs or symptoms of psoriasis.

24. The method of claim 23 wherein the GBS toxin has a purity of at least approximately 90%.

25. The method of claim 28 wherein the GBS toxin provides biological activity as evidenced by induction of respiratory distress in a sheep assay or activation of complement and binding to neovasculature in a peroxidase-antiperoxidase assay of a tumor tissue specimen.

* * * * *